(12) United States Patent
Cazzini et al.

(10) Patent No.: US 8,021,406 B2
(45) Date of Patent: Sep. 20, 2011

(54) THERMOREGULATORY DEVICE WITH ABSORBENT MATERIAL

(75) Inventors: Karl Cazzini, Orchard Park, NY (US); Joel T. Jusiak, Holland, NY (US)

(73) Assignee: Gaymar Industries, Inc., Orchard Park, NY (US)

( * ) Notice: Subject to any disclaimer, the term of this patent is extended or adjusted under 35 U.S.C. 154(b) by 1677 days.

(21) Appl. No.: 11/305,070

(22) Filed: Dec. 16, 2005

(65) Prior Publication Data

US 2007/0142887 A1 Jun. 21, 2007

(51) Int. Cl.
*A61F 7/00* (2006.01)
(52) U.S. Cl. ........................ 607/104; 607/114
(58) Field of Classification Search ............ 607/96, 607/104, 107–112, 114; 606/1, 20–29; 604/46, 604/183, 187, 217
See application file for complete search history.

(56) References Cited

U.S. PATENT DOCUMENTS

| | | | |
|---|---|---|---|
| 4,106,477 A | 8/1978 | Feld | |
| 4,844,072 A * | 7/1989 | French et al. | 607/104 |
| 5,700,284 A | 12/1997 | Owens | |
| 5,730,721 A | 3/1998 | Hyatt et al. | |
| 6,432,125 B2 | 8/2002 | Kohout | |
| 6,517,510 B1 * | 2/2003 | Stewart et al. | 604/31 |
| 6,718,785 B2 | 4/2004 | Bieberich | |
| 6,770,064 B1 | 8/2004 | Ruscher | |
| 7,041,122 B2 * | 5/2006 | Paolini et al. | 607/107 |
| 7,048,976 B2 | 5/2006 | Caceres et al. | |
| 7,077,858 B2 | 7/2006 | Fletcher et al. | |
| 2008/0132976 A1 | 6/2008 | Kane et al. | |
| 2008/0255644 A1 | 10/2008 | Carson | |
| 2008/0269852 A1 | 10/2008 | Lennox et al. | |
| 2009/0163984 A1 | 6/2009 | Robinson et al. | |
| 2009/0222072 A1 | 9/2009 | Robinson et al. | |
| 2009/0287280 A1 | 11/2009 | Wong et al. | |
| 2009/0312823 A1 | 12/2009 | Patience et al. | |
| 2010/0211139 A1 | 8/2010 | Pierre et al. | |

* cited by examiner

*Primary Examiner* — Ahmed M Farah
(74) *Attorney, Agent, or Firm* — Warner Norcross & Judd LLP

(57) ABSTRACT

The present invention is directed to a thermoregulatory device. The device has a first layer, a second layer, an enclosure, an inlet and a liquid absorbing material. The first layer has a first interior surface, and a first exterior surface. The second layer has a second interior surface and a second exterior surface. The enclosure is formed by sealing and/or attaching the first interior surface to the second interior surface. The inlet directs a liquid into the enclosure. The liquid absorbing material is positioned (a) at and/or near an aperture that allows a liquid to contact the liquid absorbing material; or (b) on the first exterior surface that is of a material that allows the liquid to contact the liquid absorbing material. In addition, the application is directed a method of using the thermoregulatory device to transfer the liquid's thermal energy from the enclosure to a patient's skin.

33 Claims, 4 Drawing Sheets

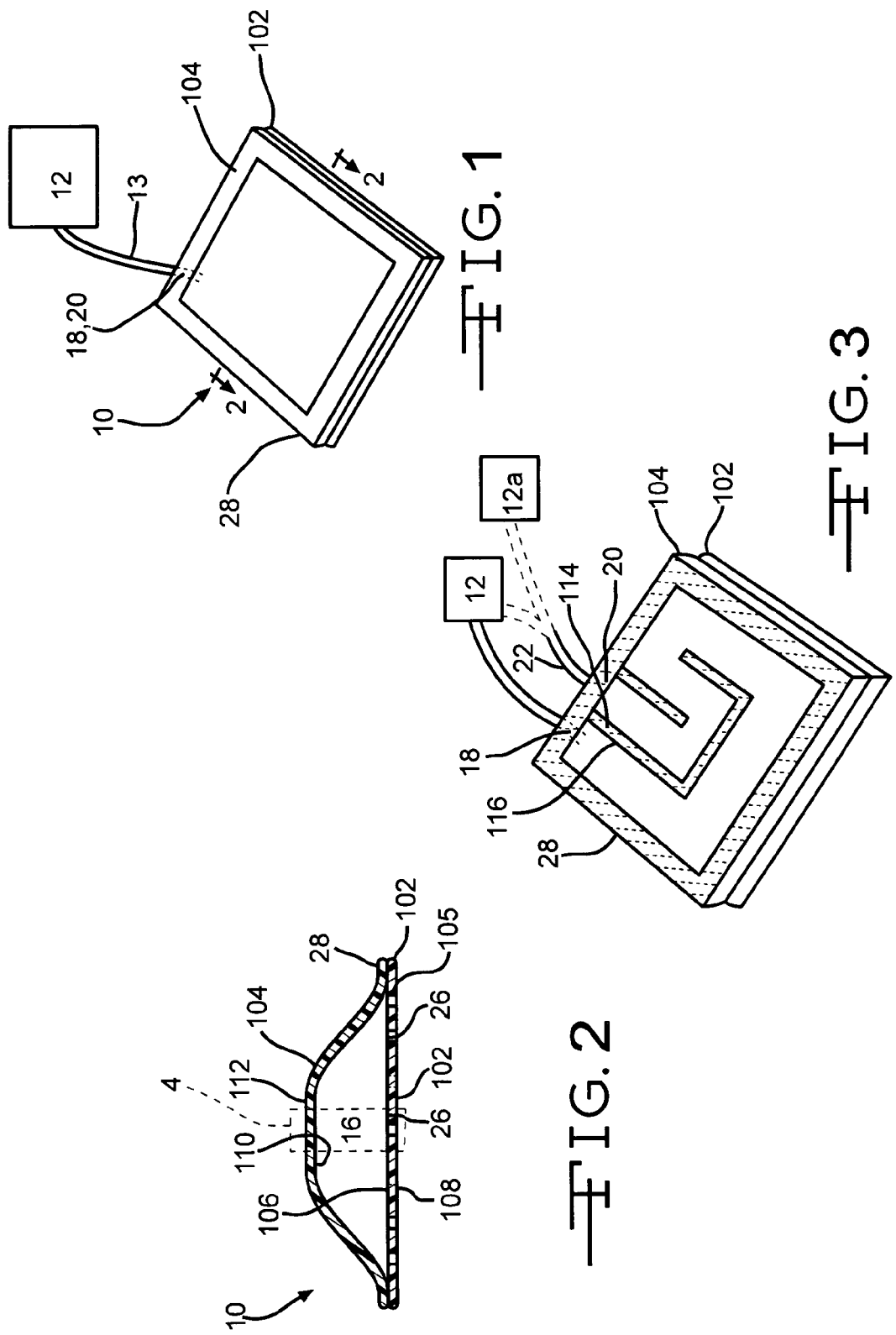

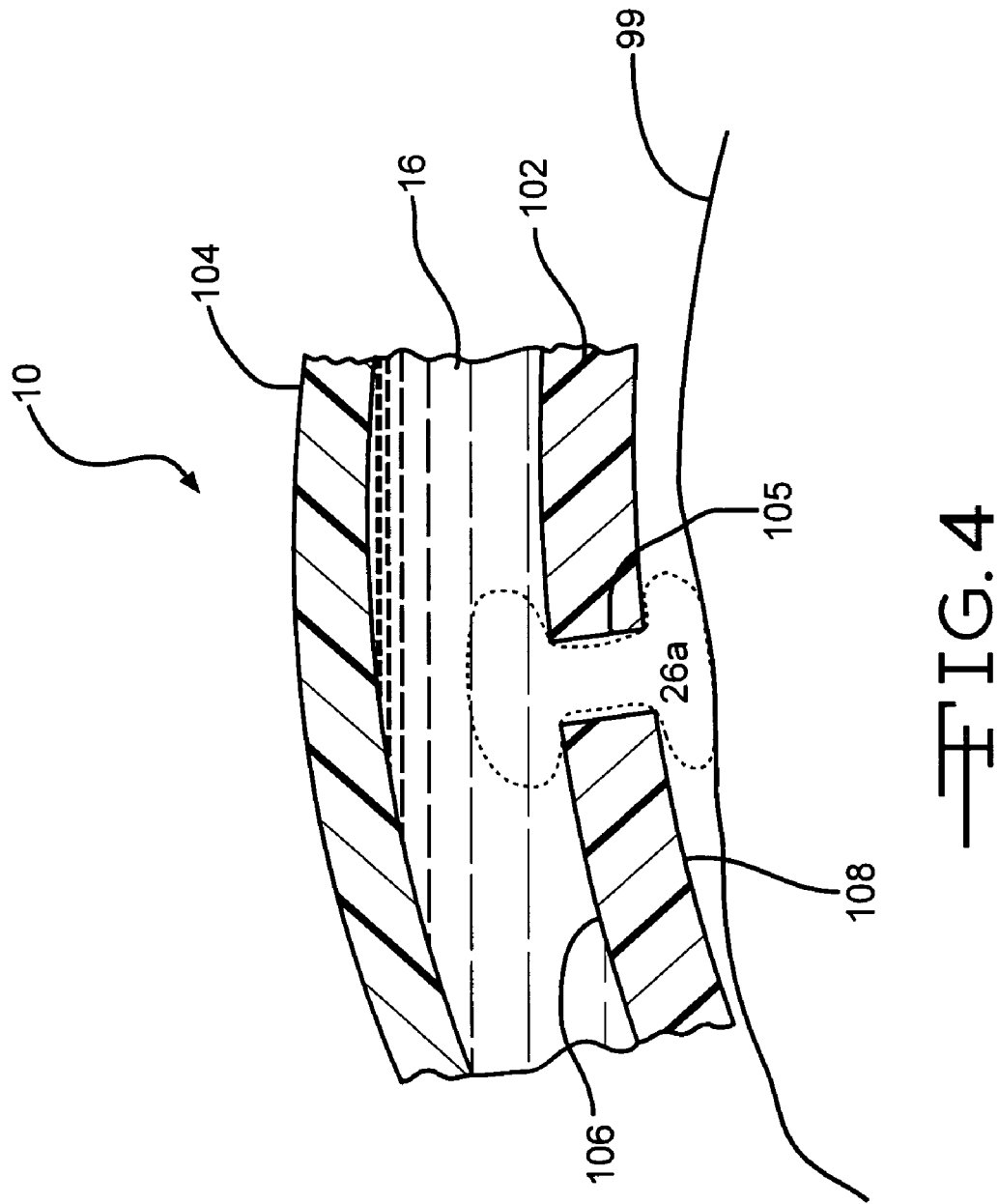

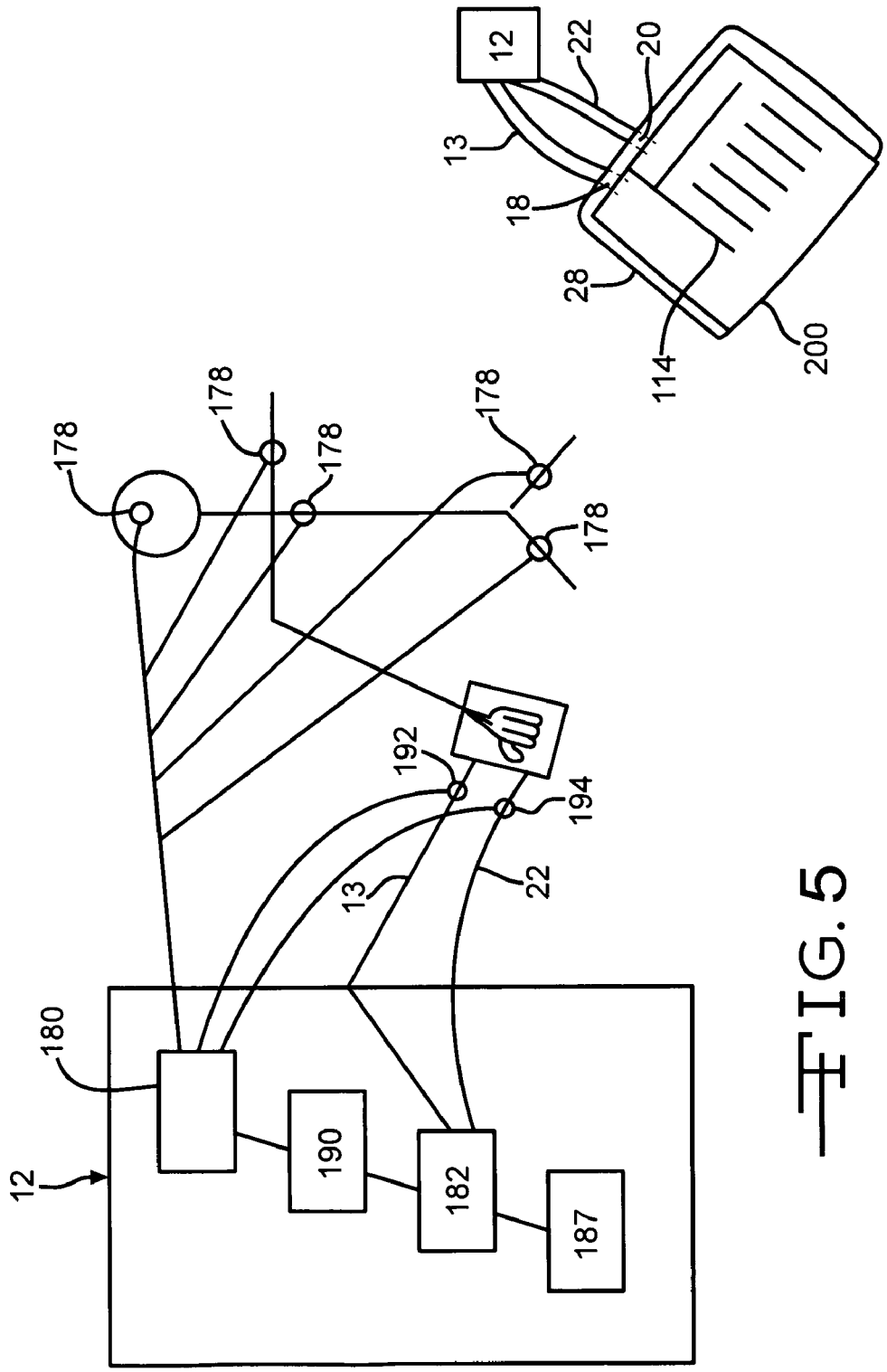

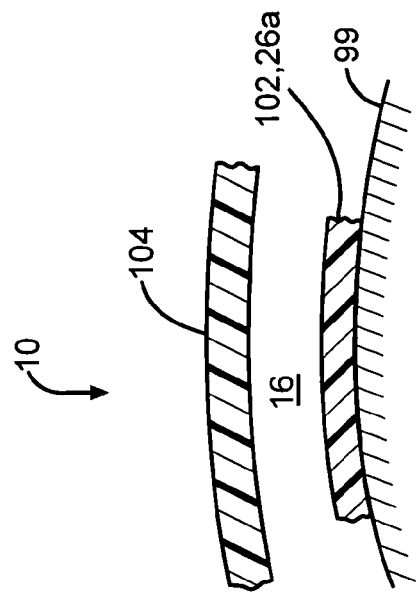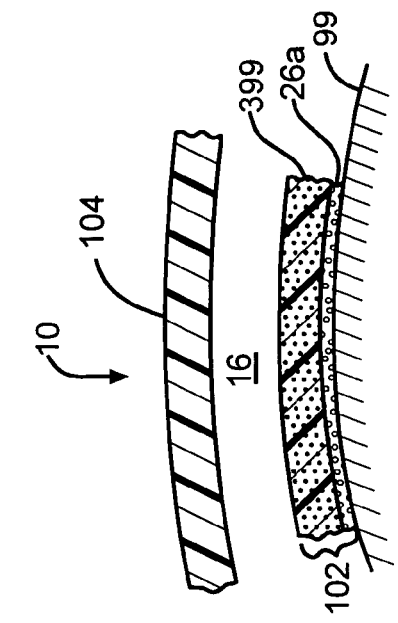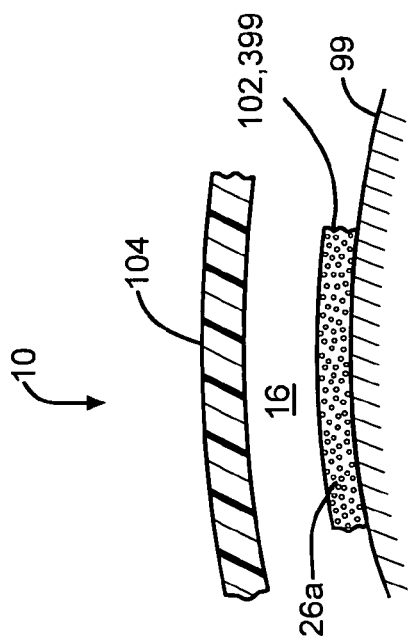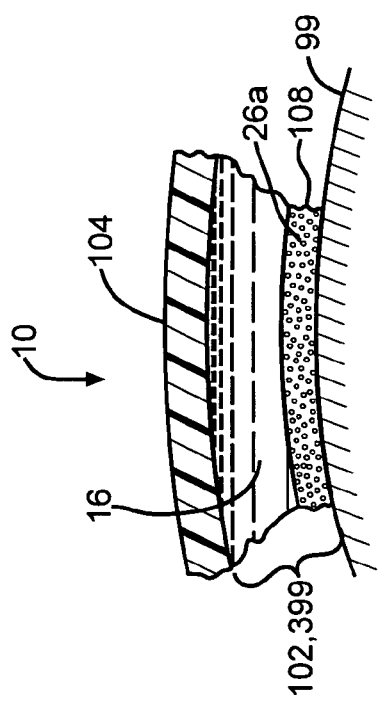

THERMOREGULATORY DEVICE WITH ABSORBENT MATERIAL

FIELD OF THE INVENTION

The present invention is directed to a thermoregulatory device. The thermoregulatory device is applied to a patient to alter the patient's temperature and/or maintain the patient's temperature.

BACKGROUND OF THE INVENTION

There are numerous types of thermoregulatory devices that alter and/or maintain a patient's temperature. One type of thermoregulatory device is Gaymar's T-pad device which has been existence since at least 1985. Gaymar's T-pad thermoregulatory device has a first polymeric layer and a second polymeric layer. The first polymeric layer has a first interior surface and a first exterior surface. Likewise, the second polymeric layer has a second interior surface and a second exterior surface.

The perimeter of the first interior surface attaches and/or seals to the perimeter of the second interior surface to form an enclosure. The enclosure receives a fluid from a fluid regulatory device. An example of a fluid regulatory device is Gaymar's Medi-Therm fluid regulatory device. The fluid regulatory device contains and/or obtains a fluid. The fluid can be any fluid that can have its temperature safely altered to a predetermined temperature. Examples of such fluids include air and water. Once the fluid is within the fluid regulatory device, the fluid regulatory device alters the fluid's temperature to a predetermined temperature.

The predetermined temperature can be normothermic to the patient's present temperature, hypothermic to the patient's present temperature, and/or hyperthermic to the patient's present temperature. The method in which the fluid is altered to the predetermined temperature is known to those of ordinary skill in the art since Gaymar's Medi-Therm fluid regulatory device has been an industry standard for more than 10 years. Accordingly, the technology by which the fluid is maintained and/or adjusted to the predetermined temperature is clearly disclosed in the prior art.

The fluid having a predetermined temperature traverses through an inlet conduit from the fluid regulatory device to an inlet of the enclosure. The fluid circulates within the enclosure. The enclosure can be an open area or contain a channel that circulates the fluid in a predetermined direction.

The channel is formed by sealing and/or attaching a preselected portion of the first interior surface to a corresponding pre-selected portion of the second interior surface. The channel design can be serpentine, counter-clockwise, counter-serpentine, clockwise, random, finger-like projections, or combinations thereof. The objective of the channel is to maximize the chance that the fluid will transfer its thermal energy to the patient in an effective manner through the entire enclosure.

If the fluid is limited to air, the fluid can be released from the enclosure through apertures. The apertures direct the air having the predetermined temperature toward the patient. The use of apertures is referred to as a low-air loss embodiment. The low-air loss embodiment effectively transfers the gas' thermal energy to the patient. Thermoregulatory devices having apertures are also referred to as convective devices. An example of a convective device is Gaymar'S Thermacare blanket systems. Gaymar's Thermacare blanket systems have been publicly available since at least 1994.

If the fluid is a liquid, the liquid normally does not enter the enclosure having apertures. Apertures allow liquids to spill on the patient. Spilling liquids on a patient is undesirable. Normally, if the thermoregulatory device's enclosure contains an aperture when the fluid is a liquid, then the thermoregulatory device is normally thrown in the garbage.

Assuming the thermoregulatory device's enclosure receives a liquid and the enclosure has no apertures, the liquid's thermal energy transfers to the patient through the polymeric layer that contacts the patient. That thermal energy should alter and/or maintain the patient's temperature toward the predetermined temperature. Obviously, some thermal energy is lost when the thermal energy passes through the polymeric layer.

To address this loss of thermal energy in the non-apertured embodiment of the thermoregulatory device, it has been proposed to position a rivet-like device into the polymer layer that contacts the patient. The rivet-like device would have one end exposed to the liquid in the enclosure and the other end would be exposed to the exterior surface of the thermoregulatory device. In most instances, the rivet-like devices should have a greater conductivity than the polymeric layer. Thereby the fluid's thermal energy should transfer to the patient's skin at a higher rate of efficiency when compared to the conventional non-apertured polymeric thermoregulatory device.

A problem with the rivet-like device is the liquid normally leaks. Manufacturing a rivet containing thermoregulatory device has numerous quality control issues. It is difficult to manufacture a thermoregulatory device with numerous apertures and each aperture being filled with a rivet-type device that does not leak. As previously stated, a thermoregulatory device that leaks a liquid onto a patient is undesirable.

SUMMARY OF THE INVENTION

The present invention is directed to a thermoregulatory device. The device has a first layer, a second layer, an enclosure, an inlet and a liquid absorbing material. The first layer has a first interior surface, and a first exterior surface. The second layer has a second interior surface and a second exterior surface. The enclosure is formed by sealing and/or attaching the first interior surface to the second interior surface. The inlet directs a liquid into the enclosure. The liquid absorbing material is positioned (a) at and/or near an aperture that allows a liquid to contact the liquid absorbing material; or (b) on the first exterior surface that is of a material that allows the liquid to contact the liquid absorbing material. In addition, the application is directed a method of using the thermoregulatory device to transfer the liquid's thermal energy from the enclosure to a patient's skin.

BRIEF DESCRIPTION OF THE FIGURES

FIG. 1 is an isometric view of the present invention.
FIG. 2 is a cross-sectional view of FIG. 1 taken along the lines 2-2.
FIG. 3 is an alternative view of FIG. 1.
FIG. 4 is an enlarged view of FIG. 2 taken from box 4 and positioned upon a patient.
FIG. 5 is a schematic of the present invention.
FIG. 6 is an alternative embodiment of FIG. 1.
FIGS. 7 to 10 are alternative embodiments of the present invention in relation to FIG. 4.

DETAILED DESCRIPTION OF THE PRESENT INVENTION

The present invention is directed to a thermoregulatory device 10 interconnected to a fluid regulatory device 12 as illustrated in FIG. 1. The fluid regulatory device 12 provides a fluid having a predetermined temperature through a first conduit 13 to the thermoregulatory device 10. For this application, the fluid is a liquid and it is understood the fluid can also be a gas.

As illustrated in FIG. 2, the thermoregulatory device 10 has a first layer 102 and a second layer 104. The first layer 102 has a first interior surface 106 and a first exterior surface 108. The second layer 104 has a second interior surface 110 and a second exterior surface 112.

For this application, the first layer 102 contacts a patient. Since the first layer 102 contacts the patient, the first layer 102 has at least one aperture 105, preferably a plurality. If the fluid is a liquid, the liquid normally leaks from the apertures 105. To decrease leaking, a liquid-absorbing material 26 is positioned within and/or near the apertures 105. The term near means the liquid-absorbing material 26 can be positioned on the first interior surface 106 and/or the first exterior surface 108 so long as the liquid contacts the liquid-absorbing material 26. The liquid-absorbing material 26 can be in a powdered form, a granulated form, a block form, a non-woven form, a woven form, or a particulate form.

The first layer 102 and the second layer 104 can be the same material or different materials. The materials can be any type of material that allows a liquid to contact the liquid absorbing material 26. Examples of such materials include and are not limited to polymeric materials, metallic materials, woven materials, foam material non-woven materials and combinations thereof.

For one embodiment, the first layer 102 and/or the second layer 104 can even be the liquid absorbing material 26 as illustrated in FIG. 9.

The second interior surface 110 and the first interior surface 106 attach and/or seal together to form an enclosure 16. Preferably, the second interior surface 110 and the first interior surface 106 attach and/or seal together at or near (a) the perimeter 28 of the second interior surface 110 and (b) the perimeter of the first interior surface 106 to obtain the largest possible enclosure 16. The sealing and/or attaching can be accomplished by heat, sound, adhesives and combinations thereof.

Alternatively, the enclosure 16 has channels 114 as illustrated in FIG. 3. The channels 114 operate in the same manner as disclosed in the background of the invention.

Reverting to FIGS. 1 and 3, the enclosure 16 contains an inlet 18. The inlet 18 receives the conduit 13. The first conduit 13 directs the liquid having a predetermined temperature into the enclosure 16. The liquid circulates in the enclosure 16. The enclosure 16 and/or channels 114 direct the liquid to an outlet 20. The outlet 20 can be (a) a separate unit in relation to the inlet 18 as illustrated in FIG. 3 or (b) inlet 18 as illustrated in FIG. 1.

If the outlet 20 is a separate unit as illustrated in FIG. 3, the liquid is directed from the outlet 20 into a second conduit 22. The second conduit 22 directs the liquid to the fluid regulatory device 12 or to another location 12a away from the patient.

If the outlet 20 is inlet 18 as illustrated in FIG. 1, the liquid is directed from the outlet 20 into the first conduit 13. The first conduit 13 directs the liquid to the fluid regulatory device 12.

How the Invention Works

The thermoregulatory device 10 is applied to a patient as illustrated in FIG. 4. The liquid enters the enclosure 16. Once in the enclosure the liquid contacts the liquid-absorbing material 26. The liquid-absorbent material 26 rapidly absorbs the contacted liquid. When the liquid is absorbed by the liquid-absorbent material 26, the liquid-absorbent material 26 enlarges and swells in size and forms a fluff or gel-like consistency. This increase in volume of liquid-absorbent material 26 may run as high as 60 to 80 times the original volume. As illustrated in FIG. 4, the enlarged liquid-absorbent material 26a plugs the apertures 105.

When the enlarged liquid-absorbent material 26a plugs the apertures 105, the enlarged material 26a is exposed to the first interior surface 106 and the first exterior surface 108. The enlarged liquid-absorbent material 26a is formed due to the liquid being trapped in the liquid absorbent material 26.

The trapped liquid in the enlarged liquid-absorbent material 26a acts as a conduit for the non-trapped fluid's thermal energy to pass through to the patient's skin 99. Since the liquid is trapped in the enlarged liquid-absorbent material 26a the liquid does not leak. Thus the only thing that should pass to the patient is the desired thermal energy.

Liquid Absorbent Material 26

The liquid absorbing material 26 is preferably sodium polyacrylate having the formula $(C_3H_3O_2Na)_n$ and variations thereof. A version of the liquid absorbing material 26 is obtainable under the trademark Water lock J-550 from Grain Processing Corporation. This material is a free-flowing powder having the ability to absorb or immobilize large volumes of aqueous solutions including dilute alkalis, dilute acids and body fluids. The liquid absorbing material 26 will absorb and immobilize 650 milliliters of water per gram of material or 75 milliliters of 1% sodium chloride solution per gram of material. The liquid absorbing material 26 will perform the foregoing absorbing and immobilizing in about 25 seconds.

Other versions of the liquid absorbing material 26 are sold under the trademark (a) Labsorb made by Lab Safety Supply Co.; and (b) Sorbaset made by Conmark, Inc.

The liquid absorbing material 26, 26a has been used extensively for different applications. Some of the alternative applications include and are not limited to diapers, and shipping containers. For both diapers and shipping containers, the liquid absorbing material has been used to contain biohazardous materials like urine or blood. The inventors are unaware of the liquid absorbing material being used as a conduit to transfer a fluid's thermal energy from one location to another, as set forth in this application.

Thermoregulatory Device 10

The thermoregulatory device 10 can be shaped into numerous designs. One design could be a blanket. Another embodiment is a pad. Other embodiments include and are not limited to a neck collar, a vest, a head gear apparatus, a glove design, a mitten design, a hand, a foot, a thigh pad, a thorax pad, a back pad, a forehead pad, a facial pad, a spinal pad, an abdomen pad, and combinations thereof. Other embodiments include bedding material, seating materials, and any other cushion material. In addition, any of these designs can have perforations therein to expose one section of the patient's body while allowing other parts of patient's body to remain covered by the thermoregulatory device 10. Those perforations 116 could be positioned along the channel 114 and the perimeter 28 as illustrated in FIG. 3.

Alternatively, the first layer 102 and the second layer 104 do not have to be discrete materials but a single unitary material. The first layer 102 can be same material folded over at edge 200 and sealed at the other perimeter ends 28 as illustrated in FIG. 6.

An alternative embodiment of the thermoregulatory device 10 having a single unitary material is accomplished when the device 10 is molded and/or machined. When the device 10 is molded and/or machined, the device 10 continues to have the first layer 102 and the second layer 104. The device 10 continues to have those layers because when the device 10 is positioned on a patient's chest then the layer that contacts a patient is the first layer 102 and the other layer that does not contact the patient is the second layer 104. Accordingly, the first layer 102 and the second layer 104 are attached together in accordance with this invention even when the device 10 is molded, machined and/or even cylindrical.

In a preferred embodiment, the first layer 102 is a material that allows the enlarged liquid-absorbent material 26a to contact the patient and the second layer 104 is normally an impermeable material. The impermeable material decreases the chances of the fluid leaking onto the patient.

In another alternative embodiment, the first layer can be made of a foam material 399 (a) coated with the liquid absorbing material as illustrated in FIG. 10, (b) with the liquid absorbing material impregnated throughout the foam material as illustrated in FIG. 7, (b) with liquid absorbing material impregnated in a first portion of the foam material that is at and/or near first exterior surface 108 and a second portion of the foam material that can be or be part of the enclosure 16 as illustrated in FIG. 8. These alternative embodiments of foam have apertures that allow the fluid to contact the liquid absorbing material but not the classical aperture design as illustrated in FIG. 4.

Fluid Regulatory Device 12

The fluid regulatory device 12 further has means for monitoring the patient's temperature as illustrated in FIG. 5. The monitoring system has sensors for monitoring the temperature of each portion of the patient's body that desires to be monitored. The sensors 178 are attachable to a corresponding part of the patient's body and connected to a monitoring and control unit 180. The monitoring and control unit 180 is connected with a device which automatically adjusts the temperature of the fluid, for example a thermostat 190. The thermostat 190 is connected to a pump 182. The pump 182 controls the supply of the liquid provided to (and in some cases from) the thermoregulatory device 10 from the liquid reservoir 187. The thermostat 190 adjusts the temperature of the liquid in a reservoir 184, depending on the temperature readings obtained from the sensors 178.

The monitoring means further includes a first liquid temperature sensor 192 arranged in the supply line 13 and possibly a second liquid temperature sensor 194 arranged in the return line 22. The sensors 192, 194 sense the temperature of the liquid in two separate liquid circulating means and supply corresponding signals to the monitoring and control unit 180, in which signals these temperatures are processed and used for controlling, for example, the thermostat 19 for correspondingly cooling, heating, or maintaining the liquid supply from the liquid reservoir 187. Controlling the liquid to the device 10 is commonly referred to as programmed therapy. As indicated, programmed therapy is an alternative embodiment of the present invention.

While in the foregoing we have disclosed an embodiment of the invention in considerable detail for purposes of illustration, it will be understood by those skilled in the art that many of these details may be varied without departing from the spirit and scope of the invention.

The invention claimed is:

1. A thermoregulatory device comprising a first layer having a first interior surface, a first exterior surface and an aperture that extends from the first interior surface to the first exterior surface;
    a second layer having a second interior surface and a second exterior surface;
    an enclosure formed by sealing and/or attaching the first interior surface to the second interior surface;
    an inlet directs a liquid into the enclosure;
    a liquid absorbing material positioned within said enclosure at and/or near the aperture.

2. The thermoregulatory device of claim 1 wherein the liquid absorbing material is a sodium polyacrylate compound.

3. The thermoregulatory device of claim 1 wherein when the liquid contacts the liquid absorbing material the liquid absorbing material expands creating a liquid trapped absorbing material.

4. The thermoregulatory device of claim 3 wherein the liquid trapped absorbing material plugs the aperture and is exposed to the first interior surface and the first exterior surface.

5. The thermoregulatory device of claim 3 wherein the liquid trapped absorbing material is a conduit for the thermal energy of the liquid, not trapped in the absorbing material and contained in the enclosure, to pass through to a patient's skin.

6. The thermoregulatory device of claim 1 wherein the liquid has a predetermined temperature.

7. The thermoregulatory device of claim 6 wherein the predetermined temperature can be normothermic to a patient's present temperature, hypothermic to the patient's present temperature, and/or hyperthermic to the patient's present temperature.

8. The thermoregulatory device of claim 1 wherein the first layer and the second layer are discrete materials.

9. The thermoregulatory device of claim 8 wherein the discrete materials are the same material selected from the group consisting of polymeric materials, metallic materials, woven materials, foam material, non-woven materials and combinations thereof.

10. The thermoregulatory device of claim 8 wherein the discrete materials are different materials selected from the group consisting of polymeric materials, metallic materials, woven materials, foam material, non-woven materials and combinations thereof.

11. The thermoregulatory device of claim 1 wherein the enclosure contains a channel.

12. The thermoregulatory device of claim 11 wherein the channel is perforated.

13. The thermoregulatory device of claim 1 wherein the thermoregulatory device is shaped in a design selected from the group consisting of a blanket; a design to fit on a patient's neck, head, hand, foot, thigh, thorax, back, forehead, face, spine, abdomen, and combinations thereof; a mattress; a cushion; and combinations thereof.

14. A thermoregulatory device comprising a first layer having a first interior surface, a first exterior surface and an aperture that extends from the first interior surface to the first exterior surface;
    a second layer having a second interior surface and a second exterior surface;
    an enclosure formed by sealing and/or attaching the first interior surface to the second interior surface;
    an inlet directs a liquid into the enclosure;
    a liquid absorbing material positioned at and/or near the aperture, wherein when the liquid contacts the liquid absorbing material the liquid absorbing material expands creating a liquid trapped absorbing material, and wherein the liquid trapped absorbing material plugs the aperture and is exposed to the first interior surface and the first exterior surface.

15. The thermoregulatory device of claim 14 wherein the liquid absorbing material is a sodium polyacrylate compound.

16. The thermoregulatory device of claim 14 wherein the liquid has a predetermined temperature.

17. The thermoregulatory device of claim 16 wherein the predetermined temperature can be normothermic to a patient's present temperature, hypothermic to the patient's present temperature, and/or hyperthermic to the patient's present temperature.

18. The thermoregulatory device of claim 14 wherein the first layer and the second layer are discrete materials.

19. The thermoregulatory device of claim 18 wherein the discrete materials are the same material selected from the group consisting of polymeric materials, metallic materials, woven materials, foam material, non-woven materials and combinations thereof.

20. The thermoregulatory device of claim 18 wherein the discrete materials are different materials selected from the group consisting of polymeric materials, metallic materials, woven materials, foam material, non-woven materials and combinations thereof.

21. The thermoregulatory device of claim 14 wherein the enclosure contains a channel.

22. The thermoregulatory device of claim 21 wherein the channel is perforated.

23. The thermoregulatory device of claim 14 wherein the thermoregulatory device is shaped in a design selected from the group consisting of a blanket; a design to fit on a patient's neck, head, hand, foot, thigh, thorax, back, forehead, face, spine, abdomen, and combinations thereof; a mattress; a cushion; and combinations thereof.

24. A thermoregulatory device comprising a first layer having a first interior surface, a first exterior surface and an aperture that extends from the first interior surface to the first exterior surface;
  a second layer having a second interior surface and a second exterior surface;
  an enclosure formed by sealing and/or attaching the first interior surface to the second interior surface;
  an inlet directs a liquid into the enclosure;
  a liquid absorbing material positioned at and/or near the aperture, wherein when the liquid contacts the liquid absorbing material the liquid absorbing material expands creating a liquid trapped absorbing material, and wherein the liquid trapped absorbing material is a conduit for the thermal energy of the liquid, not trapped in the absorbing material and contained in the enclosure, to pass through to a patient's skin.

25. The thermoregulatory device of claim 24 wherein the liquid absorbing material is a sodium polyacrylate compound.

26. The thermoregulatory device of claim 24 wherein the liquid has a predetermined temperature.

27. The thermoregulatory device of claim 26 wherein the predetermined temperature can be normothermic to a patient's present temperature, hypothermic to the patient's present temperature, and/or hyperthermic to the patient's present temperature.

28. The thermoregulatory device of claim 24 wherein the first layer and the second layer are discrete materials.

29. The thermoregulatory device of claim 28 wherein the discrete materials are the same material selected from the group consisting of polymeric materials, metallic materials, woven materials, foam material, non-woven materials and combinations thereof.

30. The thermoregulatory device of claim 28 wherein the discrete materials are different materials selected from the group consisting of polymeric materials, metallic materials, woven materials, foam material, non-woven materials and combinations thereof.

31. The thermoregulatory device of claim 24 wherein the enclosure contains a channel.

32. The thermoregulatory device of claim 31 wherein the channel is perforated.

33. The thermoregulatory device of claim 24 wherein the thermoregulatory device is shaped in a design selected from the group consisting of a blanket; a design to fit on a patient's neck, head, hand, foot, thigh, thorax, back, forehead, face, spine, abdomen, and combinations thereof; a mattress; a cushion; and combinations thereof.

* * * * *